(12) United States Patent
Guest et al.

(10) Patent No.: US 6,743,254 B2
(45) Date of Patent: Jun. 1, 2004

(54) TISSUE EXPANDER WITH PROTECTION AGAINST ACCIDENTAL PUNCTURE

(75) Inventors: Robert L. Guest, Colleyville, TX (US); Anita M. Falcon, Euless, TX (US); James Harlow, Irving, TX (US); John Labarge, Lewisville, TX (US)

(73) Assignee: Mentor Corporation, Santa Barbara, CA (US)

( * ) Notice: Subject to any disclaimer, the term of this patent is extended or adjusted under 35 U.S.C. 154(b) by 189 days.

(21) Appl. No.: 10/061,533

(22) Filed: Feb. 1, 2002

(65) Prior Publication Data

US 2003/0149481 A1 Aug. 7, 2003

(51) Int. Cl.[7] .................................................. A61F 2/12
(52) U.S. Cl. ......................................................... 623/8
(58) Field of Search .............................. 623/8, 7, 11.11

(56) References Cited

U.S. PATENT DOCUMENTS

| | | | | |
|---|---|---|---|---|
| 3,619,255 A | * | 11/1971 | Lengnick ..................... 428/429 |
| 4,200,325 A | * | 4/1980 | Johnson ........................ 294/74 |
| 4,340,699 A | * | 7/1982 | Grouiller .................... 525/460 |
| 4,378,423 A | * | 3/1983 | Suezawa et al. ............. 430/303 |
| 4,428,364 A | | 1/1984 | Bartolo ........................... 128/1 |
| 4,455,691 A | * | 6/1984 | Van Aken Redinger et al. . 623/8 |
| 4,574,780 A | * | 3/1986 | Manders ...................... 128/898 |
| 5,057,262 A | * | 10/1991 | Nohr et al. .................. 264/211 |
| 5,066,303 A | | 11/1991 | Bark et al. ...................... 623/8 |
| 5,074,878 A | | 12/1991 | Bark et al. ...................... 623/8 |
| 5,120,546 A | * | 6/1992 | Hansen et al. ............... 424/449 |
| 5,133,753 A | | 7/1992 | Bark et al. ...................... 623/8 |
| 5,146,933 A | * | 9/1992 | Boyd ........................... 128/899 |
| 5,204,436 A | * | 4/1993 | Kishita et al. ................. 528/15 |
| 5,260,123 A | * | 11/1993 | Hergenrother et al. ....... 442/183 |
| 5,401,566 A | * | 3/1995 | Magee et al. ................ 442/136 |
| 5,480,430 A | | 1/1996 | Carlisle et al. ................. 623/8 |
| 5,597,584 A | * | 1/1997 | Bhatt et al. .................. 424/486 |
| 5,632,777 A | | 5/1997 | Petrick ......................... 623/11 |
| 5,653,757 A | | 8/1997 | Petrick ......................... 623/11 |
| 5,725,507 A | | 3/1998 | Petrick ......................... 604/201 |
| 5,935,362 A | | 8/1999 | Petrick ......................... 156/165 |
| 6,060,639 A | | 5/2000 | Petrick ......................... 623/11 |

* cited by examiner

Primary Examiner—David J. Isabella
(74) Attorney, Agent, or Firm—Fish & Richardson P.C.

(57) ABSTRACT

The mammary prostheses of the invention have a self-sealing area in the upper pole region of the anterior face. The self-sealing area is greater than that of a traditional filling port, and reduces the severity of the consequences of an inadvertent puncture by a hypodermic needle during the filling process. Also, this self-sealing area is thicker than the material in the other areas of the prosthesis, causing fluid introduced to the prosthesis to stay in the lower pole region of the prosthesis, making the shape of the prosthesis appear more like that of a natural breast.

13 Claims, 2 Drawing Sheets

TISSUE EXPANDER WITH PROTECTION AGAINST ACCIDENTAL PUNCTURE

TECHNICAL FIELD

This invention relates to implantable tissue expanders and prostheses, and more particularly to implantable mammary soft tissue expanders and prostheses.

BACKGROUND

Tissue expanders are devices that are implanted beneath the skin and then gradually inflated to stretch the overlying tissue. Such expanders are used to create a pocket for receiving a permanent prosthesis and to generate an increased skin surface area so that skin can be utilized for grafting or reconstruction.

Implantable tissue expanders are commonly formed of a silicone polymer shell. After implantation, saline or some other fluid is periodically injected into the expander, for example, through an injection port, by a needle that pierces the overlying skin. In addition, the shell can be partially filled with fluid or gel prior to implantation.

A tissue expander can be provided with an injection port, for example, a port comprising a septum, that can be pierced with a hypodermic needle for the introduction of fluid into the expander. However, it can be difficult to accurately locate the injection port through the overlying tissue. If the injection port is missed and the needle punctures the shell of the tissue expander, the expander can leak. Most often, this requires that the expander be removed and replaced. This problem can be addressed by providing an injection port that is remote from the tissue expander, but is in fluid communication with the expander. Such systems are described in U.S. Pat. No. 4,190,040. Other solutions include eliminating the need for an injection site altogether by forming the expander with a self-sealing shell that can be pierced with a hypodermic needle at any point for the purpose of adding fluid to the shell. For example, U.S. Pat. No. 5,066,303 describes an expander formed using a self-sealing shell material that reportedly can be safely pierced in any location.

SUMMARY

The tissue expander of the present invention contains a self-sealing area surrounding an injection port. This self-sealing area reduces the risk of causing a leak in the expander when the hypodermic needle used to fill the expander misses the injection port. This feature reduces the frequency with which expanders require removal due to leakage caused by inadvertent punctures.

The invention features a mammary tissue expander comprising a shell having an anterior face and a posterior face, the anterior face having an upper pole portion and lower pole portion meeting at an apex, the prosthesis comprising a self-sealing material bonded to the shell within the upper pole of the anterior face of the shell to create a self-sealing region of the expander that is self-sealing after needle puncture. The expander can further comprise a injection port located within the self-sealing region of the expander.

In certain embodiments, the self-sealing material bonded to the shell acts to permit controlled directional expansion of the expander, self-sealing material is a unitary body comprising at least one layer of fabric and at least one layer of elastomeric material impregnated with a swelling agent, the fabric restraining expansion of the elastomeric material, at least a portion of the outer surface of the shell is textured, shell comprises silicone, the fabric is a knitted fabric, the fabric is a woven fabric, the fabric is a non-woven or spun-bonded fabric, the fabric is a crocheted fabric, the fabric is a polyester fabric, the swelling agent is dimethylpolysiloxane, the self-sealing material comprises at least two layers of fabric and at least two layers of elastomeric material, and the self-sealing material comprises at least two layers of fabric and at least three layers of elastomeric material.

The invention also features an improved method for introducing a swelling agent into an assembly comprising at least one layer of fabric and at least one layer of elastomeric material, the method comprising: a) providing an assembly comprising at least one layer of fabric bonded to at least one layer of elastomeric material; and b) immersing the assembly in a swelling agent under conditions of reduced atmospheric pressure for a time sufficient to allow the swelling agent to enter the at least a portion of the elastomeric material. In certain embodiments, the elastomeric material is silicone and the swelling agent is dimethylpolysiloxane.

The details of one or more embodiments of the invention are set forth in the accompanying drawings and the description below. Other features, objects, and advantages of the invention will be apparent from the description and drawings, and from the claims. All of the patents and references cited herein are hereby incorporated by reference in their entirety.

DESCRIPTION OF DRAWINGS

Like reference symbols in the various drawings indicate like elements.

DETAILED DESCRIPTION

The invention features a tissue expander having a self-sealing region surrounding an injection port. As noted above, practitioners sometimes have difficulty accurately locating the injection port of a tissue expander through the overlying tissue. On occasion, a practitioner will accidentally pierce the implant shell in the region surrounding the injection port with the filling needle, causing leakage or rupture of the expander. The self-sealing region provided in the expander of the present invention reduces the risk of leakage and rupture associated with accidental puncture of the region of the shell surrounding the injection port. Moreover, because the self-sealing region is created by applying to the shell one or more layers of a material that is relatively resistant to stretching, the self-sealing region (and injection port) can be located so as to control the extent and location of the expansion of the tissue expander. For example, in the case of a tissue expander used to create a pocket for the implantation of a mammary prosthesis, the injection port and accompanying self-sealing region can be located in the upper portion of the expander. Such an expander will have an upper portion that is relatively resistant to expansion compared to the lower portion of the expander. As a result, upon filling of the expander, greater expansion will occur in the lower portion of the expander resulting in a filled expander that more closely resembles a natural breast.

Figure 1:
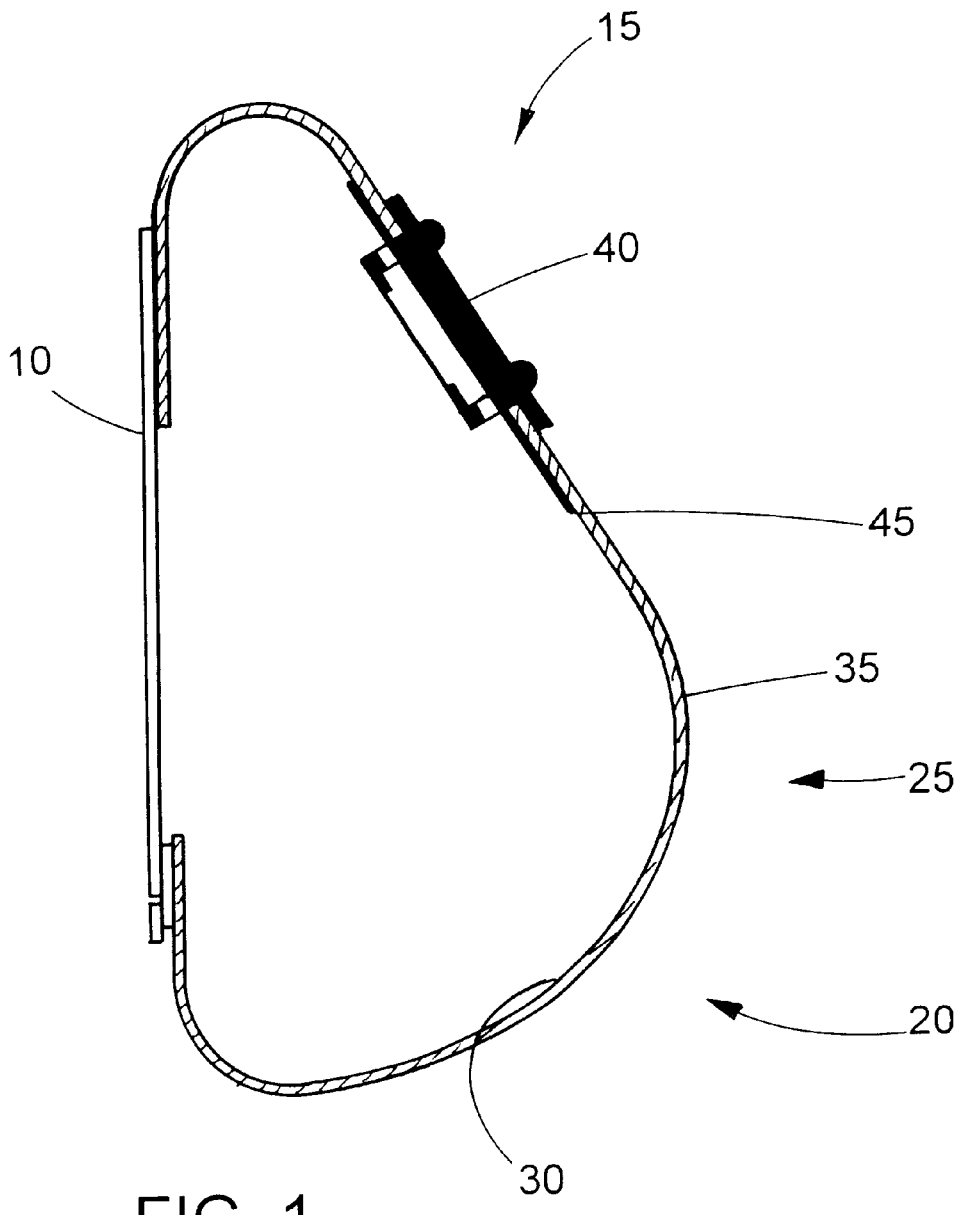
FIG. 1 is a cross-sectional side view of an embodiment of the invention.

FIG. 1 shows a cross-sectional side view of a mammary tissue expander according to one embodiment of the invention. The expander has an anterior face region 5, a posterior face region 10 that is placed against the patient's chest wall, an upper pole region 15 (i.e., the upper portion of the shell when the implant recipient is standing) a lower pole region 20 (i.e., the lower portion of the shell when the implant recipient is standing), and an apex 25 (corresponding to the point at which the nipple would be in a natural breast) separating the upper pole region and the lower pole region. The shell of the implant 27 has an inner surface 30 and an outer surface 35. The implant includes an injection port or valve 40 and a self-sealing shield 45 that located on the interior surface of the shell 30 in the upper pole region 15 of the anterior face of the expander, surrounding the filling port 40 and defining a self-sealing region that encompasses the area of the shell containing the self-sealing shield 45 and filling port 40.

The self-sealing shield is made from elastomeric material that is reinforced with a cloth or metal fabric that resists elongation in at least in one direction. Preferably the fabric is significantly stretchable in only one direction. Generally, the self-sealing shield includes at least one layer of fabric and at least one layer or elastomeric material adhered together. The fabric, (e.g., Dacron), which is generally has at least one stretch resistant axis is bonded to an elastomeric material (e.g., silicone sheeting). Preferably, at least two layers of fabric bonded to silicone sheeting are adhered to each other such that the axis that resists stretching in one layer of fabric is perpendicular to the axis that resists stretching in the other layer of fabric. Even more preferably, at least two layers of fabric, each sandwiched between two layers of silicone sheeting are bonded together to form the self-sealing shield. The shield can also be formed of a layer of non-stretchable material (e.g., a spun bonded material, e.g., Tyvek) adhered to silicone sheeting. The resulting shield is substantially resistant to stretching in all directions. The self-sealing shield is then exposed to and takes up an agent (e.g., dimethylpolysiloxane) that causes the elastomeric material to swell. The inability of the shield to stretch (due to the layer or layers of fabric) creates compressive forces within the shield as solvent is absorbed and the elastomeric material swells. The resulting forces are sufficient to seal around a small object, such as a hypodermic needle, penetrating the self-sealing shield and to reseal the area of penetration when the object is removed. When the self-sealing shield is adhered to the inner or outer surface of the shell in the region surrounding the injection port a self-sealing region resistant to leakage caused by accidental punctures is created.

Figure 2:
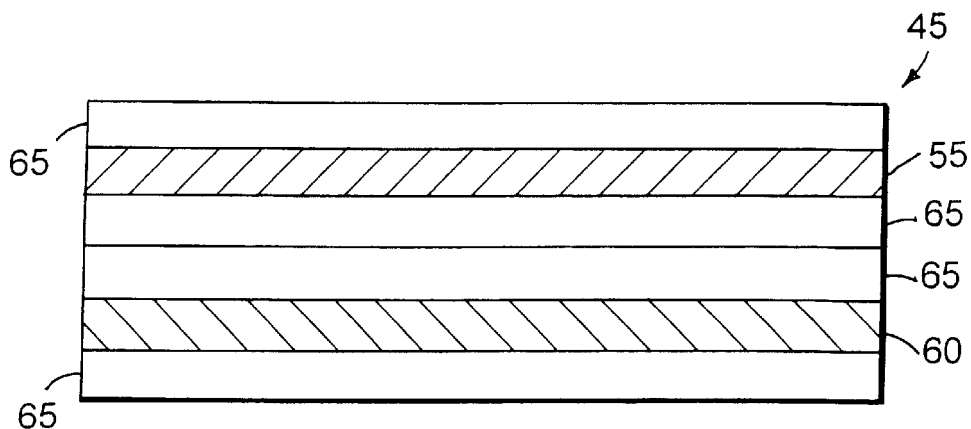
FIG. 2 is a view of the interleaving layers of fabric and elastomeric sheeting in an embodiment of a self-sealing shield.

FIG. 2 is a cross-sectional view of one embodiment of a self-sealing shield 45. This shield has two layers of fabric. The first layer of fabric 55 is oriented such that its stretch resistant axis is perpendicular to the stretch resistant axis of the second layer of fabric 60. Each layer of fabric is sandwiched between two layers of silicone sheeting 65. Thus, there are four layers of silicone sheeting.

The self-sealing shield is relatively resistant to stretching compared to the shell of the tissue expander and is generally thicker than the shell of the implant. As a result, the self-sealing area resists expansion upon filling of the implant compared to other portions of the shell. In the case of a breast tissue expander in which the self-sealing shield is positioned in the upper pole region of the expander, the fluid injected into the expander during the filling process is forced toward the lower pole region of the expander, creating a shape more closely resembling that of a natural breast.

Figure 3:
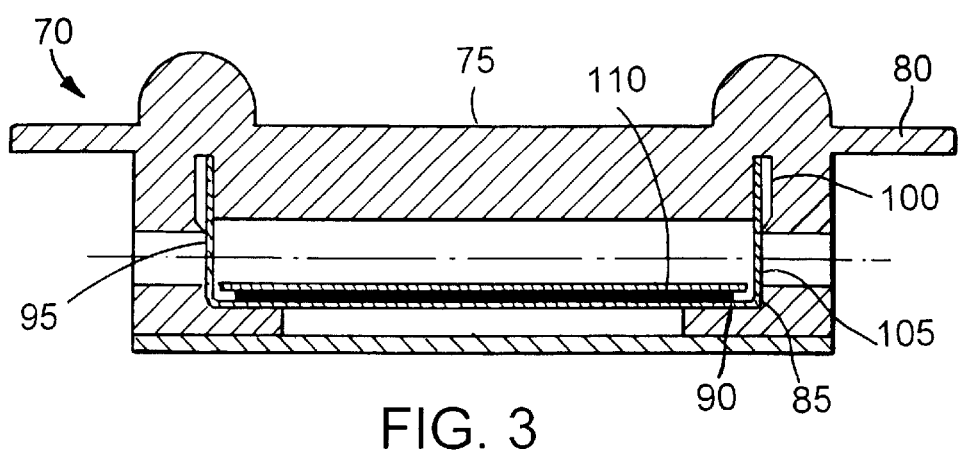
FIG. 3 is a view of an embodiment of an injection port.

FIG. 3 is a cross-sectional view of the injection port 50. The function of the injection port is to allow controlled introduction and removal of fluid to and from the tissue expander. Generally, this is accomplished through use of a hypodermic needle that pierces a selected region of the injection port, e.g., septum region of the injection port. The injection port is fitted into an opening in the shell, e.g., an opening in the upper pole of the anterior face of a mammary tissue expander. The dome 70 of the injection port is formed of an elastomeric material. The injection region 75 of the dome 70 is the central portion of the upper surface of the dome 70. The injection region is self-sealing, preventing the leaking of fluid from the implant after removal of the needle from the injection port. A flange 80 extends around the upper edge of the dome 70. This flange rests against the outer face of the shell of the expander and provides a surface for securely attaching the assembled injection port to the shell. In order to prevent accidental puncture of the posterior face of the prosthesis, the injection port is equipped with a needle guard 85 in the form of a metal cup. The needle guard has a base portion 90 and a rim portion 95. The rim portion 95 is fitted into to an annular slot 100 in the underside of the dome 70. When the rigid needle guard is inserted into the slot in the dome, compressive force is exerted on the elastomeric material of the central portion of the dome. As a result of these forces, the central portion of the dome, including the injection region 75 is self-sealing. Openings 105 in the rim of the needle guard 85 allow fluid to pass to the interior of the expander. A needle damper 110 formed of a resilient material, e.g., polysulfone, is positioned on top of the base 90 of the needle guard to prevent damage to the needle tip should the needle be insert so far as to actually strike the needle guard. It is important to reduce the risk of damage to the needle because a bent tip could tear a hole in the dome upon withdrawal of the needle. The needle damper is adhesively fastened to the needle guard.

The filling port can be modified in various ways to help the medical professional locate accurately locate it beneath the skin of the recipient. For example, the dome can include a raised "palpation" ridge that encircles the actual injection region. The injection port can be provided with a magnet, e.g., a magnet attached to the needle guard, that allows the injection port to be located by passing a device capable of locating a magnetic field over the patient's skin.

The shell of the tissue expander of the invention can have any desired shape any thickness that is suitable for the purpose of the particular expander. The shell may be single lumen or multi-lumen and is commonly formed of a biocompatible elastomer, e.g., silicone. Dip molding using an appropriately sized and shaped mandrel can be used to form the shell. The mandrel is dipped into silicone dispersion and then removed to allow partial cure or solvent evaporation. The process is generally repeated several times. Once the shell has been formed it is removed from the mandrel. (Other methods such as injection molding or spraying may also be used to form the shell.)

This dip molding process results in the formation of a partial shell that has an opening, e.g., a circular hole (patch hole) in its posterior face. The self-sealing shield is applied to the inner or outer surface of the shell, e.g., in the region that will surround the injection port. The injection port is installed and the patch hole is subsequently covered with a patch that seals the hole, thus forming a complete, fluid impervious shell. The patch is attached to the partial shell using silicone rubber or other similar biocompatible adhesive. The completed shell can either be non-filled or partially pre-filled. After implantation, the expander is intraoperatively filled through an injection fill port or valve with saline, gel, foam, or combinations of these materials or other suitable materials known in the art to gradually expand the tissue expander to the desired dimensions.

EXAMPLE 1

The self-sealing shield is made using sheets of woven polyester fabric sandwiched between layers of silicone sheeting. Woven polyester fabric such as Dacron® is layered on unvulcanized silicone sheeting, having a thickness of about 0.018 to about 0.022 inches, and passed through calender rollers, then rolled and oven cured. A layer of unvulcanized silicone sheeting is applied to the polyester fabric using calender rollers. This process results in the production of an assembly consisting of a layer of woven polyester fabric sandwiched between a layer of fully cured silicone and a layer of uncured silicone. This assembly can be significantly stretched in only one direction. Two such assemblies are stacked on top of each other such that the machining direction of the fabric layers are at a 90° angle and the uncured sides abut. The assemblies are cold pressed together, e.g., for about 25 to 35 seconds at about 45 to 55 psi with the unvulcanized sides of the assemblies together, forming double thickness assemblies. The double thickness assemblies are then cured, e.g., for about 25 to 35 minutes at about 320 to 330° F. The double thickness assemblies are then cut to the desired shape. It is desirable that all of the components be at room temperature (e.g., 70 to 80° F.) during the assembly process.

The double thickness assemblies are next placed in a sealed container of 1000 cp dimethylpolysiloxane fluid and subjected to 28 mm Hg. vacuum for at least 90 minutes. The vacuum is then released, and the double thickness assemblies are left to soak in the dimethylpolysiloxane fluid for about 95 to 190 hours, preferably about 96 hours. This entire process allows the silicone sheeting to become swollen with dimethylpolysiloxane. The application of a vacuum removes air and moisture from the assembly and facilitates the entry of the dimethylpolysiloxane into the silicone sheeting. The double thickness assemblies are then removed from the fluid, and the residual fluid is removed, e.g., with isopropyl alcohol. The reduced pressure during the initial soaking step greatly decreases the total time required to produce a suitable self-sealing shield. Thus, the total soaking time can be reduced from about 200 hours to about 96 hours.

In order to seal the double thickness assemblies, they are dip coated in dimethyl silicone dispersion and cured at about 110 to 140° F. for about 10 to 14 minutes; dip coated in diphenyl silicone dispersion and cured at about 110 to 140° F. for about 10 to 14 minutes; and then dip coated in dimethyl silicone dispersion and cured at about 110 to 140° F. for about 10 to 14 minutes. The double thickness assemblies are then fully cured by holding at about 185 to 250° F. for about 10 to 14 minutes and then at about 265 to 325 2° F. for about 55 to 65 minutes. This process completes the production of a self-sealing shield. The complete self-sealing shield is approximately 0.068 to 0.078 inches thick, preferably 0.075 inches thick.

EXAMPLE 2

An elastomeric shell with an filling port and a surrounding self-sealing area is formed by first preparing an elastomeric shell and then adhering to it a self-sealing material of having an area larger than the injection port. An elastomeric shell is formed by conventional dip molding in silicone dispersion using an appropriately sized and shaped mandrel. After an appropriate thickness is achieved, the shell is cured. The shell will generally have an opening on its posterior face in order to strip it off the mandrel.

All or a portion of the outer surface of the shell can be textured in order to reduce capsular contraction and provide other desirable properties. For example, a layer of unvulcanized or partially vulcanized silicone sheeting can be applied to outer surface of the anterior face of the implant. A layer of porous or textured material is then layered above the unvulcanized or partially vulcanized silicone sheeting and the assembly is compressed using cold press or hot press platens. After compression, the porous or textured material is removed, leaving a textured imprint on the silicone sheeting. Subsequently the now textured shell is fully cured. A suitable process is described in Yan and Purkait, U.S. Pat. No. 4,960,425.

The textured shell is then turned inside out and stretched over an appropriately shaped and sized disk that allows the perimeter of the shell to lie smooth. The self-sealing shield is attached to the upper pole region of the elastomeric shell, for example, by placing a sheet of uncured silicone sheeting between the self-sealing shield and the inner surface of the shell and then compressing the self-sealing shield, uncured silicone sheeting and shell between heated plates for about 35 to 55 seconds at ambient temperature. The assembly is then post-cured for about 45 to 75 minutes at about 315 to 335° F.

EXAMPLE 3

A die is used to cut a hole through the shell and self-sealing shield to accommodate the injection port. The injection port, for example an injection port similar to that depicted in FIG. 3 is then secured to the shell in a manner that allows the complete expander to be fluid-tight. For example, a sheet of uncured silicone sheeting is place between the flange of the injection port and the outer surface of the shell. An appropriately shaped press is then used to compress the flange portion of the injection port, the uncured silicone sheeting and shell for about 2 minutes ±10 seconds at about 340 to 360° F.

A number of embodiments of the invention have been described. Nevertheless, it will be understood that various modifications may be made without departing from the spirit and scope of the invention. For example, an embodiment wherein the self-sealing area is the filling means. The expander can additionally contain a needle stop having a peripheral shape that substantially corresponds to the posterior face of the prosthesis and is formed of a needle impenetrable, non-corrosive material such as titanium or stainless steel. (See, e.g., U.S. Pat. No. 5,133,753). The self-sealing shield can also be produced as in a manner similar to the self-sealing injection button described in U.S. Pat. No. 4,428,364.

What is claimed is:

1. A mammary tissue expander comprising a shell having an anterior face and a posterior face, the anterior face having an upper pole portion and lower pole portion meeting at an apex, the prosthesis comprising an injection port having a self-sealing septum region, the injection port being located within the upper pole of the anterior face of the shell and a self-sealing material bonded to the shell within the upper pole of the anterior face defining a self-sealing shield region substantially surrounding the injection port.

2. The tissue expander of claim 1 where the self-sealing material bonded to the shell acts to permit controlled directional expansion of the expander.

3. The tissue expander of claim 1 wherein the self-sealing material is a unitary body comprising at least one layer of fabric and at least one layer of elastomeric material impregnated with a swelling agent, the fabric restraining expansion of the elastomeric material.

4. The tissue expander of claim 1 wherein at least a portion of the outer surface of the shell is textured.

5. The tissue expander of claim 1 wherein the shell comprises silicone.

6. The tissue expander of claim 4 wherein the fabric is a knitted fabric.

7. The tissue expander of claim 3 wherein the fabric is a woven fabric.

8. The tissue expander of claim 3 wherein the fabric is a non-woven or spunbonded fabric.

9. The tissue expander of claim 3 wherein the fabric is a crocheted fabric.

10. The tissue expander of claim 3 wherein the fabric is a polyester fabric.

11. The tissue expander of claim 3 wherein the swelling agent is dimethylpolysiloxane.

12. The tissue expander of claim 3 wherein the self-sealing material comprises at least two layers of fabric and at least two layers of elastomeric material.

13. The tissue expander of claim 3 wherein the self-sealing material comprises at least two layers of fabric and at least three layers of elastomeric material.

* * * * *

UNITED STATES PATENT AND TRADEMARK OFFICE
CERTIFICATE OF CORRECTION

| | | |
|---|---|---|
| PATENT NO. | : 6,743,254 B2 | Page 1 of 1 |
| APPLICATION NO. | : 10/061533 | |
| DATED | : June 1, 2004 | |
| INVENTOR(S) | : Robert L. Guest et al. | |

It is certified that error appears in the above-identified patent and that said Letters Patent is hereby corrected as shown below:

Col. 1, Line 60, "comprise a injection" should be replaced with --comprise an injection--

Col. 3, Line 25, "which is generally" should be replaced with --which generally--

Col. 4. Line 22, "into to an" should be replaced with --into an--

Col. 4, Line 38, "professional locate accurately locate it" should be replaced with --professional accurately locate it--

Col. 5, Line 55, "325 2°" should be replaced with --325°--

Col. 5, Line 62, "with an filling" should be replaced with --with a filling--

Col. 7, Line 10, "claim 4" should be replaced with --claim 3--

Signed and Sealed this

Twenty-first Day of November, 2006

JON W. DUDAS
*Director of the United States Patent and Trademark Office*